(12) United States Patent
Masuda

(10) Patent No.: US 10,494,393 B2
(45) Date of Patent: Dec. 3, 2019

(54) SILICON-CONTAINING SULFURIC ACID ESTER SALT

(71) Applicant: Nisshinbo Holdings, Inc., Tokyo (JP)

(72) Inventor: Gen Masuda, Chiba-shi (JP)

(73) Assignee: NISSHINBO HOLDINGS, INC., Tokyo (JP)

( * ) Notice: Subject to any disclaimer, the term of this patent is extended or adjusted under 35 U.S.C. 154(b) by 0 days.

(21) Appl. No.: 16/093,791

(22) PCT Filed: Mar. 7, 2017

(86) PCT No.: PCT/JP2017/009018
§ 371 (c)(1),
(2) Date: Oct. 15, 2018

(87) PCT Pub. No.: WO2017/183342
PCT Pub. Date: Oct. 26, 2017

(65) Prior Publication Data
US 2019/0127403 A1    May 2, 2019

(30) Foreign Application Priority Data
Apr. 21, 2016   (JP) .................................. 2016-085077

(51) Int. Cl.
| | | |
|---|---|---|
| C07F 7/08 | (2006.01) | |
| C07F 9/54 | (2006.01) | |
| H01G 11/62 | (2013.01) | |
| H01M 10/0567 | (2010.01) | |

(52) U.S. Cl.
CPC .............. C07F 9/5407 (2013.01); C07F 7/08 (2013.01); C07F 7/081 (2013.01); C07F 9/54 (2013.01); H01G 11/62 (2013.01); H01M 10/0567 (2013.01); *H01M 2300/0025* (2013.01)

(58) Field of Classification Search
None
See application file for complete search history.

(56) References Cited

U.S. PATENT DOCUMENTS

| | | |
|---|---|---|
| 4,725,926 A | 2/1988 | Morimoto et al. |
| 2004/0030015 A1 | 2/2004 | Chowdhury et al. |
| 2015/0203518 A1 | 7/2015 | Masuda |
| 2016/0027592 A1 | 1/2016 | Shimamoto et al. |

FOREIGN PATENT DOCUMENTS

| | | | |
|---|---|---|---|
| JP | 61-32509 A | 2/1986 | |
| JP | 62-252927 A | 11/1987 | |
| JP | 63-173312 A | 7/1988 | |
| JP | 10-55717 A | 2/1998 | |
| JP | 2010-70539 A | 4/2010 | |
| WO | 99/24120 A1 | 5/1999 | |
| WO | 2004/013218 A1 | 2/2004 | |
| WO | WO-2004013218 A1 * | 2/2004 | ........... C07C 211/63 |
| WO | 2013/005712 A1 | 1/2013 | |
| WO | 2014/163055 A1 | 10/2014 | |

OTHER PUBLICATIONS

International Search Report dated Apr. 25, 2017, issued in counterpart International Application No. PCT/JP2017/009018 (2 pages).

* cited by examiner

*Primary Examiner* — Clinton A Brooks
*Assistant Examiner* — Kofi Adzamli
(74) *Attorney, Agent, or Firm* — Westerman, Hattori, Daniels & Adrian, LLP

(57) ABSTRACT

Provided is a silicon-containing sulfuric acid ester salt comprising a silicon-containing sulfuric acid ester anion represented by formula (1) and a cation selected from cations respectively represented by formulae (2) to (5).

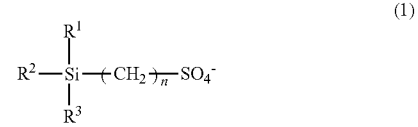

(1)

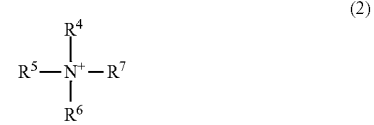

(2)

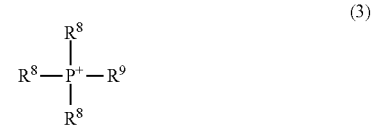

(3)

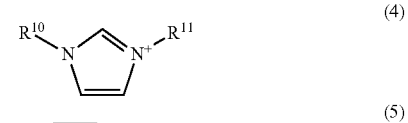

(4)

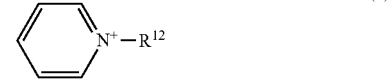

(5)

12 Claims, 7 Drawing Sheets

VOLTAGE (V)

VOLTAGE (V)

SILICON-CONTAINING SULFURIC ACID ESTER SALT

TECHNICAL FIELD

The present invention relates to a silicon-containing sulfuric acid ester salt.

BACKGROUND ART

In recent years, along with rapid proliferation of mobile electronic devices such as digital cameras, smartphones, and tablets, increasing are the demand for power storage devices such as secondary batteries which are used as power sources of these devices and can be repeatedly used by charging, and the demand for the increase of their capacity and energy density.

These power storage devices commonly include a solution of an electrolytic salt in an aprotic organic solvent as an electrolytic solution. Various combination of these electrolyte salts and aprotic organic solvents have been studied up to date. Examples of the widely used electrolytic salts include quaternary ammonium salts (Patent Documents 1 to 3) and quaternary phosphonium salts (Patent Document 4), owing to their high solubility in organic solvents and degree of dissociation, and wide electrochemical stable ranges.

However, these electrolytic salts contain halogen atoms such as fluorine atoms in anions, and thus still have problems in terms of environment load, so that these problems are expected to be solved. Additionally, the electrolytic salts for the above-described uses are demanded to have electrochemical properties such as high ion electrical conductivity and wide electric potential windows.

PRIOR ART DOCUMENTS

Patent Documents

Patent Document 1: JP-A S61-32509
Patent Document 2: JP-A S63-173312
Patent Document 3: JP-A H10-55717
Patent Document 4: JP-A S62-252927

SUMMARY OF INVENTION

Technical Problem

The present invention has been made in view of the above-described circumstances, and is intended to provide a novel silicon-containing sulfuric acid ester salt which is free of halogen atom, and is suitable as an electrolyte and an electrolytic solution for power storage devices.

Solution to Problem

As a result of dedicated research for achieving the above-described purpose, the inventor has found that a silicon-containing sulfuric acid ester salt composed of a silicon atom-containing sulfate anion and a certain monovalent cation has marked electrochemical properties, and thus completed the present invention.

That is, the present invention provides the silicon-containing sulfuric acid ester salt.

1. A silicon-containing sulfuric acid ester salt including a silicon-containing sulfate anion represented by the formula (1) and a cation selected from those represented by the formulae (2) to (5).

[Chem. 1]

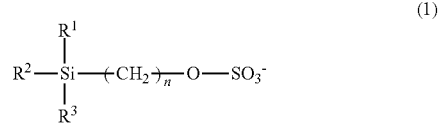

(1)

wherein $R^1$ to $R^3$ each independently represent an alkyl group having 1 to 4 carbon atoms, and n represents an integer of 2 to 4,

[Chem. 2]

(2)

(3)

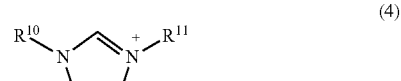

(4)

(5)

wherein $R^4$ to $R^7$ each independently represent an alkyl group having 1 to 4 carbon atoms, or an alkoxyalkyl group represented by —$(CH_2)_k$—OR, any two of $R^4$ to $R^7$ may be bonded to each other to form a ring together with a nitrogen atom to which they bond, and the remaining two may be bonded to each other to form a spiro ring wherein a spiro atom is a nitrogen atom, $R^8$ represents an alkyl group having 1 to 12 carbon atoms, $R^9$ represents an alkyl group having 1 to 20 carbon atoms, $R^{10}$ and $R^{11}$ each independently represent an alkyl group having 1 to 12 carbon atoms, or an alkoxyalkyl group represented by —$(CH_2)_k$—OR, $R^{12}$ represents an alkyl group having 1 to 12 carbon atoms, or an alkoxyalkyl group represented by —$(CH_2)_k$—OR, the symbol k represents 1 or 2, and R represents a methyl group or an ethyl group.

2. The silicon-containing sulfuric acid ester salt according to the above 1, wherein $R^1$ to $R^3$ are methyl groups.

3. The silicon-containing sulfuric acid ester salt according to the above 1 or 2, wherein n is 2 or 3.

4. The silicon-containing sulfuric acid ester salt according to any one of the above 1 to 3, wherein the cation is a quaternary ammonium ion represented by the formula (2).

5. The silicon-containing sulfuric acid ester salt according to the above 4, wherein the quaternary ammonium ion represented by the formula (2) is selected from those represented by the formulae (2-1) to (2-4).

[Chem. 3]

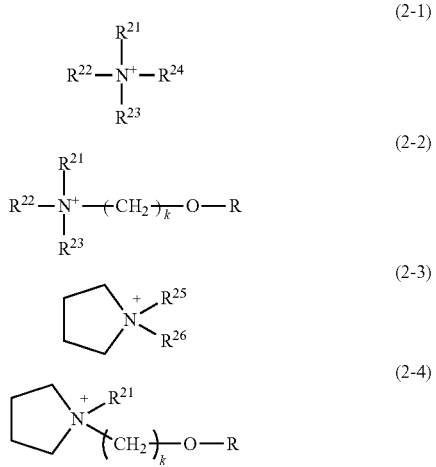

wherein R and k are the same as the above-described ones, $R^{21}$ to $R^{24}$ each independently represent an alkyl group having 1 to 4 carbon atoms, $R^{25}$ and $R^{26}$ each independently represent an alkyl group having 1 to 4 carbon atoms, and $R^{25}$ and $R^{26}$ may be bonded to each other to form a ring together with the nitrogen atom to which they bond.

6. The silicon-containing sulfuric acid ester salt according to any one of the above 1 to 3, wherein the cation is the quaternary phosphonium ion represented by the formula (3).
7. The silicon-containing sulfuric acid ester salt according to the above 6, wherein $R^8$ and $R^9$ have different structures.
8. The silicon-containing sulfuric acid ester salt according to the above 7, wherein $R^8$ is an alkyl group having 2 to 8 carbon atoms, and $R^9$ is an alkyl group having 10 to 20 carbon atoms.
9. The silicon-containing sulfuric acid ester salt according to any one of the above 1 to 3, wherein the cation is an imidazolium ion represented by the formula (4).
10. The silicon-containing sulfuric acid ester salt according to any one of the above 1 to 3, wherein the cation is a pyridinium ion represented by the formula (5).
11. An ionic liquid including the silicon-containing sulfuric acid ester salt according to any one of the above 1 to 10.
12. The ionic liquid according to the above 11, wherein a melting point is 25° C. or lower.

Advantageous Effects of Invention

The silicon-containing sulfuric acid ester salt of the present invention is halogen-free, and thus gives a small environment load. Additionally, the silicon-containing sulfuric acid ester salt of the present invention has a wider electric potential window than prior art halogen-free salts, and is electrochemically stable.

DESCRIPTION OF EMBODIMENTS

Figure 1:
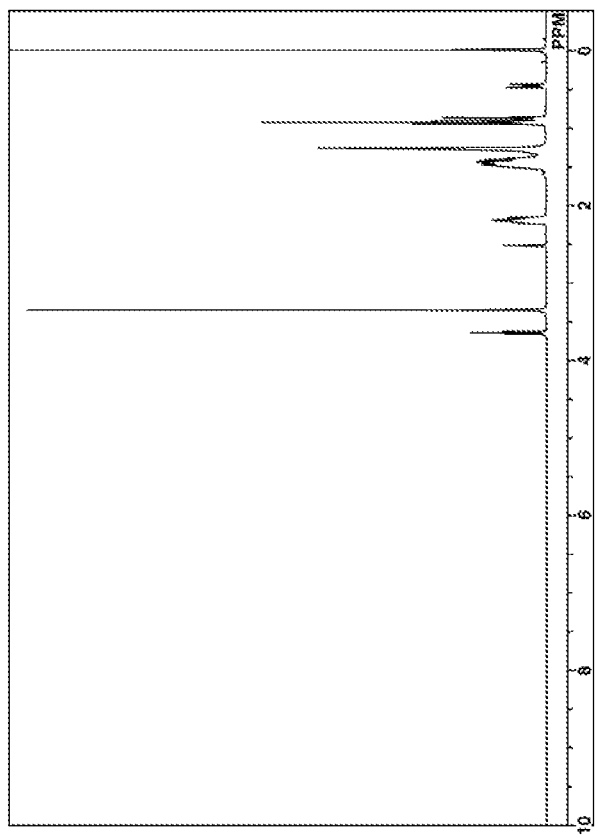
FIG. 1 is a $^1$H-NMR chart of a silicon-containing sulfuric acid ester salt 1 prepared in Example 1.

[Silicon-containing Sulfuric Acid Ester Salt]
An anion composing a silicon-containing sulfuric acid ester salt of the present invention is represented by the following formula (1).

[Chem. 4]

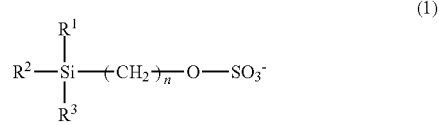

In the formula (1), $R^1$ to $R^3$ each independently represent an alkyl group having 1 to 4 carbon atoms. The alkyl group may be linear, branched, or cyclic, and its examples include a methyl group, an ethyl group, an n-propyl group, an isopropyl group, a cyclopropyl group, an n-butyl group, a sec-butyl group, an isobutyl group, a tert-butyl group, and a cyclobutyl group. Among them, $R^1$ to $R^3$ are preferably alkyl groups having 1 to 3 carbon atoms, more preferably linear alkyl groups having 1 to 3 carbon atoms, and even more preferably methyl groups or ethyl groups, and yet even more preferably methyl groups.

In the formula (1), n represents an integer of 2 to 4, and is preferably 2 or 3.

The cation composing the silicon-containing sulfuric acid ester salt of the present invention is any one selected from those represented by the following formulae (2) to (5).

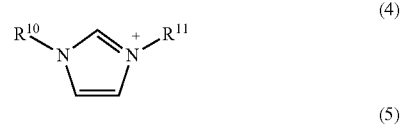

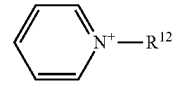

In the formula (2), $R^4$ to $R^7$ each independently an alkyl group having 1 to 4 carbon atoms, or an alkoxyalkyl group represented by —$(CH_2)_k$—OR. The symbol k represents 1 or 2. R represents a methyl group or an ethyl group.

Examples of the alkyl group having 1 to 4 carbon atoms include those listed as the examples of $R^1$ to $R^3$. Examples of the alkoxyalkyl group include a methoxymethyl group, an ethoxy methyl group, a methoxyethyl group, and an ethoxyethyl group. Among the alkoxyalkyl groups, a methoxyethyl group or an ethoxyethyl group is preferred.

Any two of $R^4$ to $R^7$ may be bonded to each other to form a ring together with the nitrogen atom to which they bond, and the remaining two may be bonded to each other to form a spiro ring wherein the spiro atom is a nitrogen atom. In this case, examples of the to ring include an aziridine ring, an azetidine ring, a pyrrolidine ring, a piperidine ring, an azepane ring, an imidazolidine ring, a pyridine ring, pyrrole ring, an imidazole ring, and a quinol ring. Among them, a pyrrolidine ring, a piperidine ring, an imidazolidine ring, a pyridine ring, a pyrrole ring, an imidazole ring, and a quinol ring are preferred, and a pyrrolidine ring and an imidazolidine ring are more preferred. The spiro ring is particularly preferably a 1,1'-spirobipyrrolidine ring.

Specific examples of the quaternary ammonium ion represented by the formula (2) include those represented by the formulae (2-1) to (2-4).

[Chem. 5]

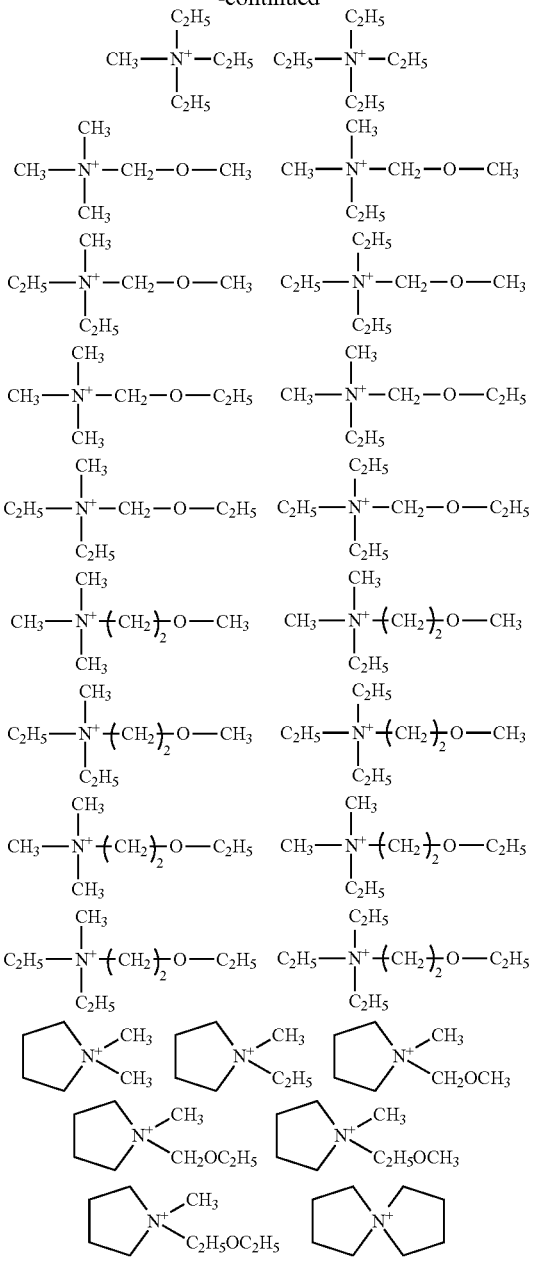

In the formulae (2-1) to (2-4), R and k represent the same ones as described above. $R^{21}$ to $R^{24}$ each independently represents an alkyl group having 1 to 4 carbon atoms. $R^{25}$ and $R^{26}$ each independently represent an alkyl group having 1 to 4 carbon atoms. The $R^{25}$ and $R^{26}$ may be bonded to each other to form a ring together with the nitrogen atom to which they bond.

Specific examples of the quaternary ammonium ion represented by the formula (2) are shown below, but not limited thereto.

[Chem. 6]

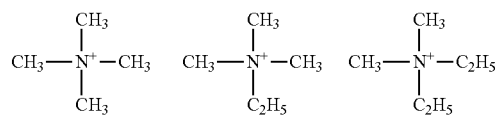

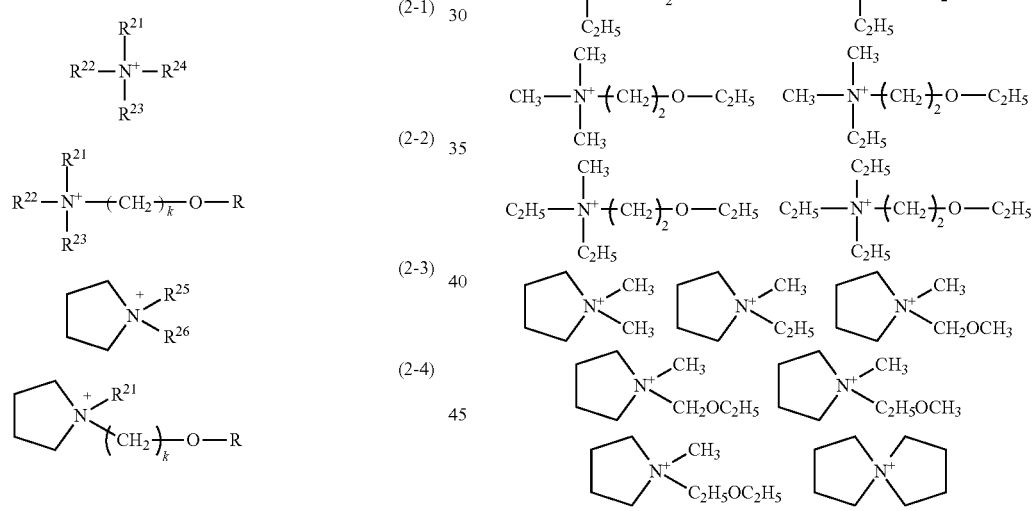

In the formula (3), $R^8$ represents an alkyl group having 1 to 12 carbon atoms. The alkyl group having 1 to 12 carbon atoms may be linear, branched, or cyclic, and its examples include the alkyl group having 1 to 4 carbon atoms described above, and an n-pentyl group, a cyclopentyl group, an n-hexyl group, a cyclohexyl group, an n-heptyl group, an n-octyl group, an n-nonyl group, an n-decyl group, an n-undecyl group, and an n-dodecyl group.

In the formula (3), $R^9$ represents an alkyl group having 1 to 20 carbon atoms. The alkyl group having 1 to 20 carbon atoms may be linear, branched, or cyclic, and its examples include the alkyl group having 1 to 12 carbon atoms described above, an n-tridecyl group, an n-tetradecyl group, an n-pentadecyl group, an n-hexadecyl group, an n-heptadecyl group, an n-octadecyl group, an n-nonadecyl group, and an n-eicosyl group.

Of the quaternary phosphonium ions represented by the formula (3), those having a structure including different $R^8$ and $R^9$ tend to form an ionic liquid. In this case, $R^8$ is preferably an alkyl group having 2 to 8 carbon atoms, more preferably an alkyl group having 3 to 8 carbon atoms, and even more preferably an alkyl group having 4 to 8 carbon atoms. Specifically, $R^8$ is preferably an n-butyl group or an n-hexyl group. $R^9$ is preferably an alkyl group having 10 to 20 carbon atoms, and more preferably an alkyl group having 12 to 20 carbon atoms.

Examples of the quaternary phosphonium ion represented by the formula (3) are shown below, but not limited thereto.

[Chem. 7]

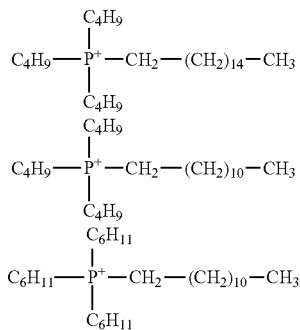

In the formula (4), $R^{10}$ and $R^{11}$ each independently represent an alkyl group having 1 to 12 carbon atoms, or an alkoxyalkyl group represented by $-(CH_2)_k-OR$. R and k are the same as those described above. Examples of the alkyl group having 1 to 12 carbon atoms include those listed as the examples of $R^8$. The alkyl group preferably has 1 to 8 carbon atoms, and more preferably has 1 to 4 carbon atoms in terms of cost. Examples of the alkoxyalkyl group include those listed as the examples of $R^4$ to $R^7$.

In the formula (5), $R^{12}$ represents an alkyl group having 1 to 12 carbon atoms, or an alkoxyalkyl group represented by $-(CH_2)_k-OR$. R and k are the same as those described above. Examples of the alkyl group having 1 to 12 carbon atoms include the same ones listed as the examples of $R^8$. The alkyl group preferably has 1 to 8 carbon atoms, and more preferably has 1 to 4 carbon atoms in terms of cost. Examples of the alkoxyalkyl group include those listed as the examples of $R^4$ to $R^7$.

The silicon-containing sulfuric acid ester salt of the present invention may be an ionic liquid depending on the type of the cation. For example, those including a cation represented by the formula (2-4) is an ionic liquid, and those represented by the formula (3) tend to be an ionic liquid when $R^8$ and $R^9$ have different structures. The ionic liquid is a salt composed solely of an ion, and generally refers to that having a melting point of 100° C. or lower. The ionic liquid including the silicon-containing sulfuric acid ester salt of the present invention is preferably in a liquid state at room temperature (25° C.).

[Method for Producing Silicon-containing Sulfuric Acid Ester Salt]

The silicon-containing sulfuric acid ester salt of the present invention can be produced by, for example, a neutralization method with an ion exchange resin using the silicon-containing sulfuric acid ester salt represented by the formula (6) and the salt represented by the formula (7).

[Chem. 8]

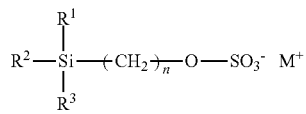

In the formula, $R^1$ to $R^3$ and n are the same as the above-described ones. $M^+$ represents an ammonium ion or a monovalent metal ion. Examples of the monovalent metal ion include $Li^+$, $Na^+$, and $K^+$. $A^+$ represents any one selected from the cations represented by the formulae (2) to (5). $X^-$ represents a halide ion. Examples of the halide ion include a fluoride ion, a chloride ion, a bromide ion, and an iodide ion. Among them, a chloride ion, a bromide ion, and an iodide ion are preferred.

The silicon-containing sulfuric acid ester salt represented by the formula (6) may be synthesized by a known method, such as the method described in Al-Horani, R. A., and Desai, U. R., Tetrahedron, 66 (2010), 2907-2918. For example, it can be readily obtained by heating a silicon-containing alcohol and amidosulfuric acid (sulfamic acid) to about 130 to 150° C. in the presence of urea. The salt represented by the formula (7) may be synthesized according to any known method, or may use any commercial product.

When the neutralization method is used, firstly, the silicon-containing sulfuric acid ester salt represented by the formula (6) and the salt represented by the formula (7) are converted to the silicon-containing sulfate and hydroxide represented by the formula (6') using a cation exchange resin and an anionic exchange resin, respectively, and they are mixed.

[Chem. 9]

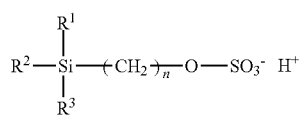

(In the formula, $R^1$ to $R^3$ and n are the same as those described above.)

When the neutralization method is used in the present invention, the counter ion is not particularly limited as long as it allows ion exchange of the silicon-containing sulfuric acid ester salt represented by the formula (6) and the salt represented by the formula (7). However, in terms of cost, the silicon-containing sulfuric acid ester salt represented by the formula (6) is preferably an ammonium salt, a sodium salt, or a potassium salt. The counter ion the salt represented by the formula (7) is preferably a halide ion, and particularly preferably a chloride ion or a bromide ion in terms of cost.

The molar ratio between the silicon-containing sulfate and the hydroxide in the neutralization reaction is not particularly limited, and may be about 5:1 to 1:5. In consideration of cost, the molar ratio is preferably close to 1:1, and it is particularly preferred that the point of reaction completion is the neutralization point of the aqueous layer.

After the completion of the reaction, ordinary aftertreatment is carried out to obtain the target object.

Examples of the other method for producing the silicon-containing sulfuric acid ester salt include ion exchange with an ion exchange resin using the silicon-containing sulfuric acid ester salt represented by the formula (6) and the salt represented by the formula (7).

Specifically, the ion exchange method is carried out as follows: firstly, an aqueous solution of the salt represented by the formula (7) is passed through a column filled with a cation exchange resin, thereby allowing the cation exchange resin to carry the cation of the salt, and the column is washed with water. Subsequently, the silicon-containing sulfuric acid ester salt represented by the formula (6) is passed through the column, the eluate is collected, and purified to obtain the desired silicon-containing sulfuric acid ester salt.

The cation exchange resin may be a commonly used cation exchange resin, but is preferably a strongly acidic cation exchange resin. They are commercially available.

[Use of Silicon-containing Sulfuric Acid Ester Salt]

The silicon-containing sulfuric acid ester salt of the present invention is useful as an electrolyte or an additive for electrolytes for power storage devices such as electric double layer capacitors, lithium ion capacitors, redox capacitors, lithium secondary batteries, lithium ion secondary batteries, lithium air batteries, and proton polymer batteries. The silicon-containing sulfuric acid ester salt of the present invention is also useful as an antistatic agent, a plasticizer, or a lubricant added to polymer materials such as rubber and plastic.

The ionic liquid including the silicon-containing sulfuric acid ester salt of the present invention is a halogen-free ionic liquid, so that is useful as a green solvent having a low impact on the environment. In particular, the ionic liquid including the silicon-containing sulfuric acid ester salt of the present invention has a wider electric potential window and is more electrochemically stable than prior art ionic liquids as well as prior art solid electrolyte salts, and thus are suitable as electrolytes and electrolytic solutions of electric storage devices.

EXAMPLES

The present invention is more specifically described below with reference to Examples, but the present invention will not be limited to the following Examples. The reagents, analyzers, and conditions used in Examples are as follows.

[1] Nuclear Magnetic Resonance ($^1$H-NMR) Spectrum
  Apparatus: AL-400, JEOL Ltd.
  Solvent: deuterium oxide, deuterated dimethyl sulfoxide or chloroform-d

[2] Melting Point
  Apparatus: DSC 6200, Seiko Instruments, Inc.
  Measurement conditions:
    The temperature was increased from 20° C. to 60° C. at a rate of 10° C. per minute, kept at 60° C. for one minute, decreased from 60° C. to −90° C. at a rate of 1° C. per minute, kept at −90° C. for one minute, and then increased from −90 to 60° C. at a rate of 1° C.

[3] Decomposition Point
  Apparatus: TG-DTA 6200, Seiko Instruments, Inc.
  Measurement conditions:
    In air atmosphere, the temperature was increased from 30 to 500° C. at a rate of 10° C. per minute, and the temperature when the weight decreased 10% was recorded as the decomposition point.

[4] Cyclic Voltammetry Measurement
  Apparatus: Electrochemical measurement apparatus HSV-100, Hokuto Denko Corporation Measurement conditions:
    The measurement was carried out at a sweeping rate of 5 mV/sec using a glassy carbon electrode as the working electrode, a platinum electrode as the counter electrode, and an Ag/Ag$^+$ type reference electrode as the reference electrode.

Example 1

Synthesis of Silicon-containing Sulfuric Acid Ester Salt 1

[Chem. 10]

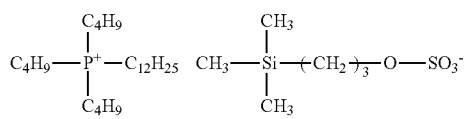

Silicon-containing sulfuric acid ester salt 1

1.0 equivalent of trimethylsilyl propanol (Sigma-Aldrich), 1.1 equivalent of amidosulfuric acid (Wako Pure Chemical Industries, Ltd.), and 0.2 equivalent of urea (Wako Pure Chemical Industries, Ltd.) were mixed in a nitrogen atmosphere, and heated to 150° C. under stirring. After the temperature reached to 150° C., heating was continued for 6 hours under stirring, and then the temperature was allowed to decrease to room temperature. To the mixture, ethyl acetate (Wako Pure Chemical Industries, Ltd.) was added until the solid thus obtained was completely immersed therein, the solid was broken with a spatula, stirring was continued for about one hour, and then the solid was isolated by filtration under reduced pressure, and dried. In this manner, the target compound A containing some urea was obtained (yield 79%).

[Chem. 11]

Compound A

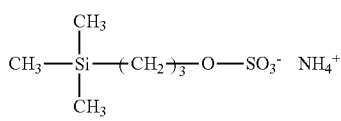

Figure 2:
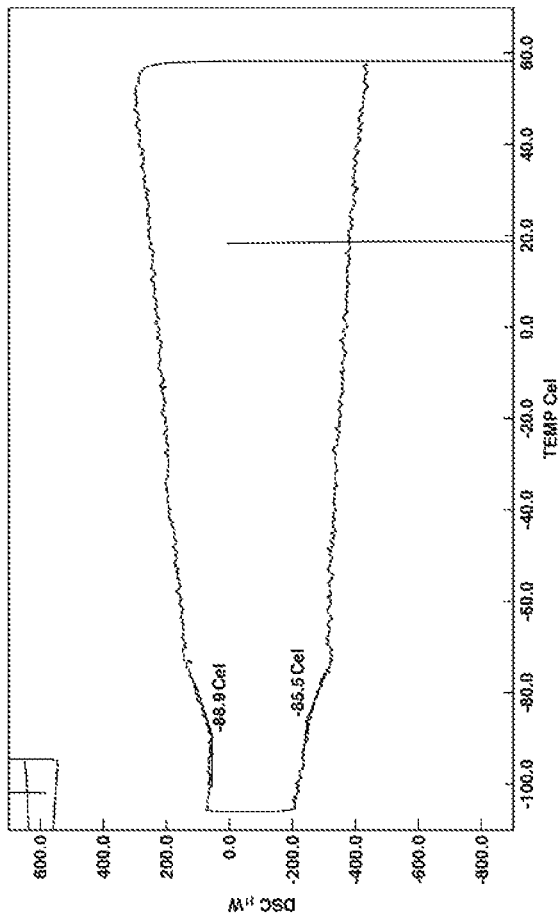
FIG. 2 is a DSC chart of the silicon-containing sulfuric acid ester salt 1 prepared in Example 1.
Figure 3:
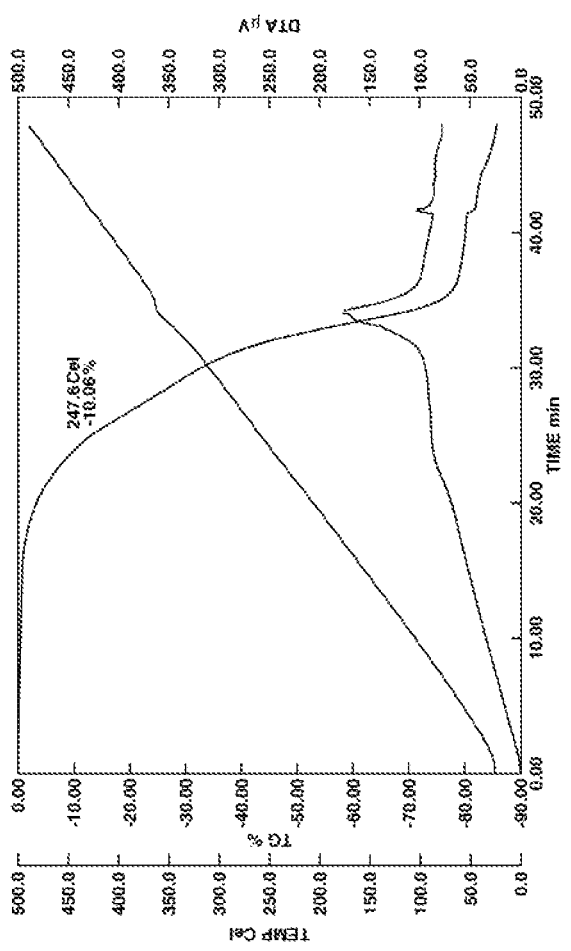
FIG. 3 is a TG-DTA chart of the silicon-containing sulfuric acid ester salt 1 prepared in Example 1.

To 1.0 equivalent of the compound A thus obtained, HISHICOLIN PX-412C (Nippon Chemical Industries Co., Ltd., 50% aqueous solution of dodecyl tributyl phosphonium chloride) was added to make the amount of dodecyl tributyl phosphonium chloride 1.0 equivalent, and the mixture was stirred for 30 minutes. To the reaction liquid in two layers, ethyl acetate (Wako Pure Chemical Industries, Ltd.) was added in the same volume with HISHICOLIN PX-412C, and further stirred for 3 hours. After standing, the aqueous layer in the lower layer was removed, and deionized water (half volume of HISHICOLIN PX-412C) and 0.15 equivalent of the compound A were added to the organic layer. After stirring for 3 hours, the liquid was separated again, and the organic layer was washed with water four times. The solvent and water were removed from the organic layer using an evaporator, and then a vacuum pump, thereby obtaining the silicon-containing sulfuric acid ester salt 1 in the form of a colorless transparent liquid (yield: 92%). The $^1$H-NMR chart (solvent: chloroform-d), DSC chart, and TG-DTA chart of the silicon-containing sulfuric acid ester salt 1 are given in FIG. 1, FIG. 2, and FIG. 3, respectively.

Example 2

Synthesis of Silicon-Containing Sulfuric Acid Ester Salt 2

[Chem. 12]

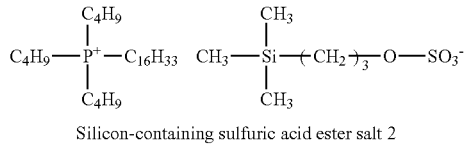

Silicon-containing sulfuric acid ester salt 2

Figure 4:
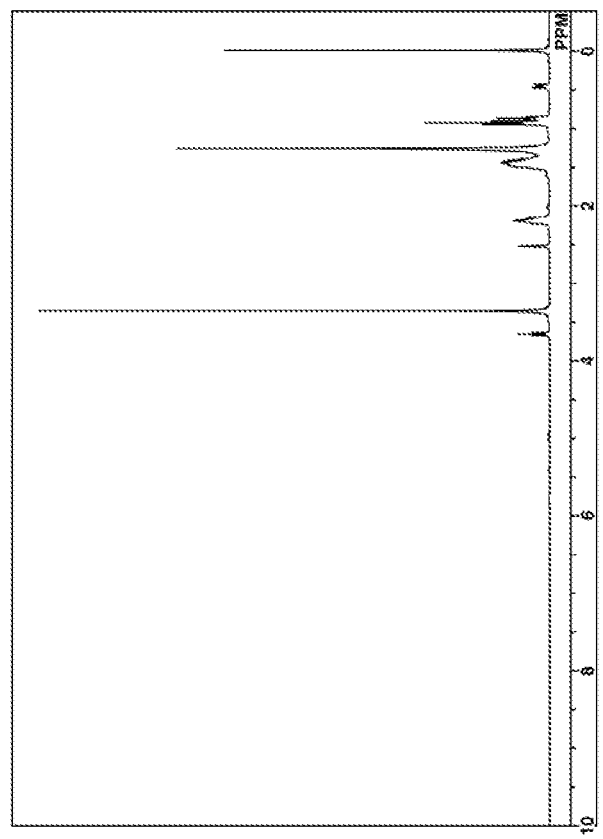
FIG. 4 is a $^1$H-NMR chart of a silicon-containing sulfuric acid ester salt 2 prepared in Example 2.
Figure 5:
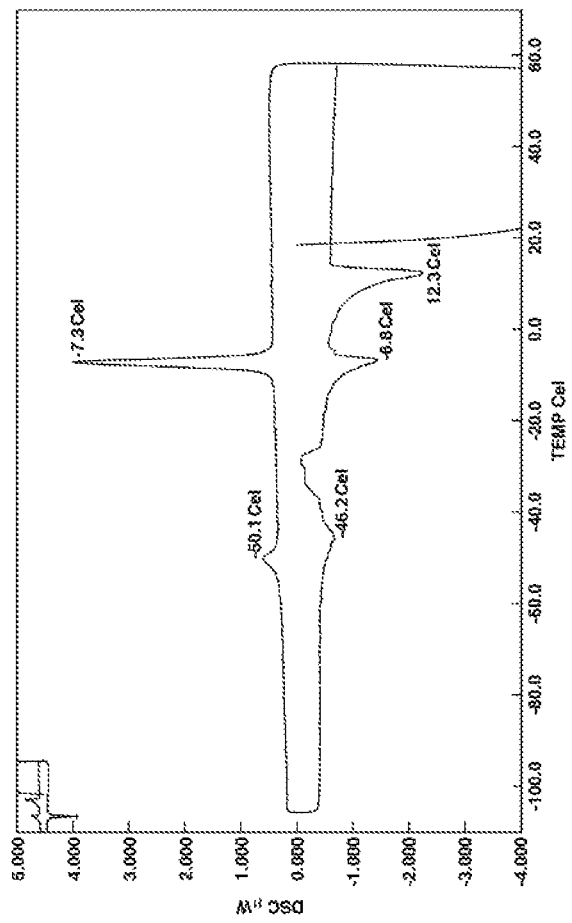
FIG. 5 is a DSC chart of the silicon-containing sulfuric acid ester salt 2 prepared in Example 2.
Figure 6:
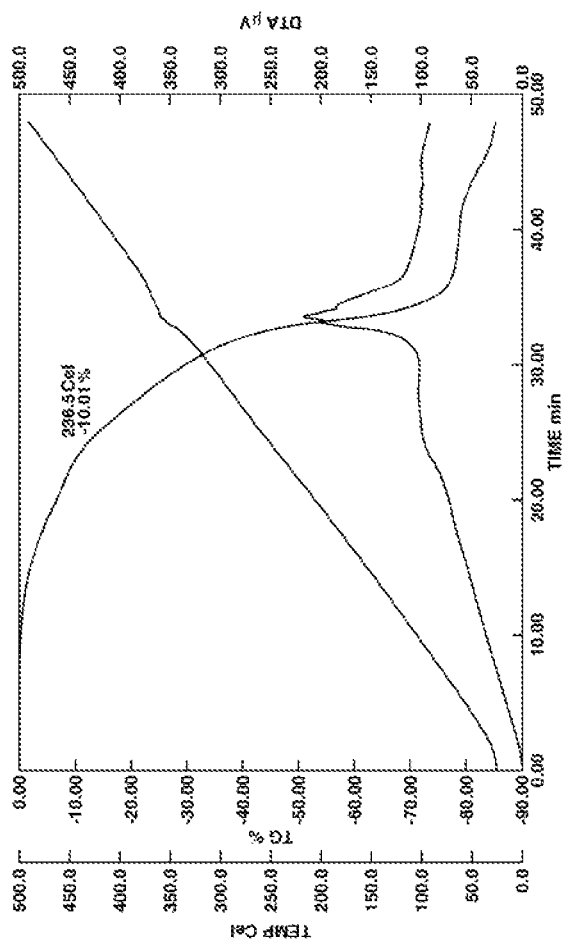
FIG. 6 is a TG-DTA chart of the silicon-containing sulfuric acid ester salt 2 prepared in Example 2.

A silicon-containing sulfuric acid ester salt 2 in the form of a colorless transparent liquid was obtained in the same manner as in Example 1 (yield 91%), except that HISHICOLIN PX-412C was replaced with HISHICOLIN PX-416C (50% aqueous solution of hexadecyl tributyl phosphonium chloride, Nippon Chemical Industries Co., Ltd.,). The $^1$H-NMR chart (solvent: chloroform-d), DSC chart, and TG-DTA chart of the silicon-containing sulfuric acid ester salt 2 are given in FIG. 4, FIG. 5, and FIG. 6, respectively.

The melting point and decomposition point (10% weight decrease, in atmosphere) of the silicon-containing sulfuric acid ester salts 1 and 2 obtained from the DSC and TG-DTA measurements are given in Table 1.

TABLE 1

| | Silicon-containing sulfuric acid ester salt | Melting point (° C.) | Decomposition point (° C.) |
|---|---|---|---|
| Example 1 | 1 | None (not observed) | 248 |
| Example 2 | 2 | 12 | 237 |

Examples 3 and 4

Measurement of Electric Potential Window

Figure 7:
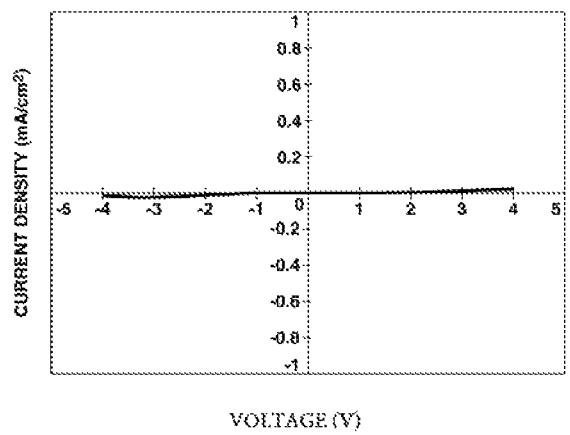
FIG. 7 illustrates a result of an electric potential window measurement of the silicon-containing sulfuric acid ester salt 1.
Figure 8:
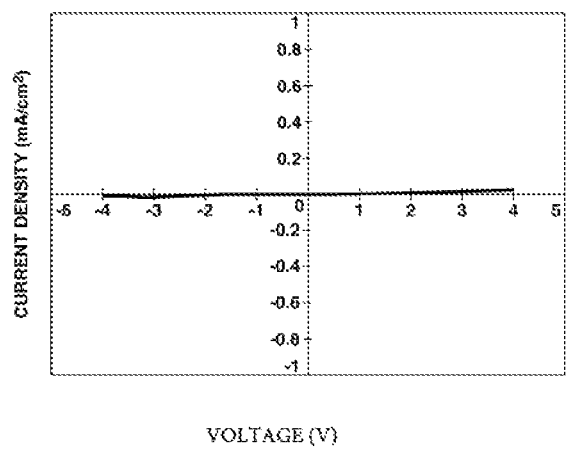
FIG. 8 illustrates a result of an electric potential window measurement of the silicon-containing sulfuric acid ester salt 2.

The silicon-containing sulfuric acid ester salt 1 (Example 3) and the silicon-containing sulfuric acid ester salt 2 (Example 4) were subjected to cyclic voltammetry measurement. The results are given in FIG. 7 (Example 3) and FIG. 8 (Example 4). As is evident from these figures, all of the silicon-containing sulfuric acid ester salts of the present invention have wide electric potential windows, indicating that they have marked electrochemical stability.

The invention claimed is:

1. A silicon-containing sulfuric acid ester salt comprising a silicon-containing sulfate anion represented by the formula (1) and a cation selected from those represented by the formulae (2) to (5),

[Chem. 1]

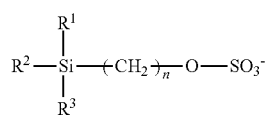

(1)

wherein $R^1$ to $R^3$ each independently represent an alkyl group having 1 to 4 carbon atoms, and n represents an integer of 2 to 4,

[Chem. 2]

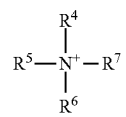

(2)

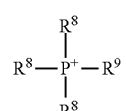

(3)

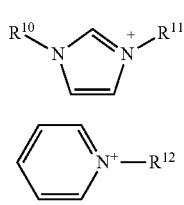

(4)

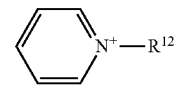

(5)

wherein $R^4$ to $R^7$ each independently represent an alkyl group having 1 to 4 carbon atoms, or an alkoxyalkyl group represented by —$(CH_2)_k$—OR, any two of $R^4$ to $R^7$ may be bonded to each other to form a ring together with a nitrogen atom to which they bond, and the remaining two may be bonded to each other to form a spiro ring wherein a spiro atom is a nitrogen atom, $R^8$ represents an alkyl group having 1 to 12 carbon atoms, $R^9$ represents an alkyl group having 1 to 20 carbon atoms, $R^{10}$ and $R^{11}$ each independently represent an alkyl group having 1 to 12 carbon atoms, or an alkoxyalkyl group represented by —$(CH_2)_k$—OR, $R^{12}$ represents an alkyl group having 1 to 12 carbon atoms, or an alkoxyalkyl group represented by —$(CH_2)_k$—OR, the symbol k represents 1 or 2, and R represents a methyl group or an ethyl group.

2. The silicon-containing sulfuric acid ester salt according to claim 1, wherein $R^1$ to $R^3$ are methyl groups.

3. The silicon-containing sulfuric acid ester salt according to claim 1, wherein n is 2 or 3.

4. The silicon-containing sulfuric acid ester salt according to claim 1, wherein the cation is a quaternary ammonium ion represented by the formula (2).

5. The silicon-containing sulfuric acid ester salt according to claim 4, wherein the quaternary ammonium ion represented by the formula (2) is selected from those represented by the formulae (2-1) to (2-4),

[Chem. 3]

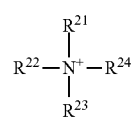

(2-1)

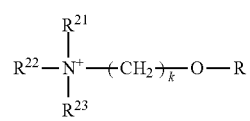

(2-2)

-continued

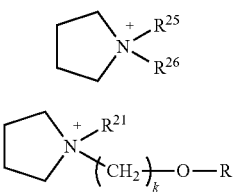

wherein R and k are the same as the above-described ones, $R^{21}$ to $R^{24}$ each independently represent an alkyl group having 1 to 4 carbon atoms, $R^{25}$ and $R^{26}$ each independently represent an alkyl group having 1 to 4 carbon atoms, and $R^{25}$ and $R^{26}$ may be bonded to each other to form a ring together with the nitrogen atom to which they bond.

6. The silicon-containing sulfuric acid ester salt, according to claim 1, wherein the cation is the quaternary phosphonium ion represented by the formula (3).

7. The silicon-containing sulfuric acid ester salt according to claim 6, wherein $R^8$ and $R^9$ have different structures.

8. The silicon-containing sulfuric acid ester salt according to claim 7, wherein $R^8$ is an alkyl group having 2 to 8 carbon atoms, and $R^9$ is an alkyl group having 10 to 20 carbon atoms.

9. The silicon-containing sulfuric acid ester salt according to clamp 1, wherein the cation is an imidazolium ion represented by the formula (4).

10. The silicon-containing sulfuric acid ester salt according to claim 1, wherein the cation is a pyridinium ion represented by the formula (5).

11. An ionic liquid comprising the silicon-containing sulfuric acid ester salt according to claim 1.

12. The ionic liquid according to claim 11, wherein a melting point is 25° C. or lower.

* * * * *